US00PP32586P2

(12) United States Plant Patent
Burton

(10) Patent No.: US PP32,586 P2
(45) Date of Patent: Dec. 8, 2020

(54) ***HEBE* 'HEBANN03'**

(50) Latin Name: *Hebe speciosa*
Varietal Denomination: HEBANN03

(71) Applicant: Steve Burton, Tamahere (NZ)

(72) Inventor: Steve Burton, Tamahere (NZ)

( * ) Notice: Subject to any disclaimer, the term of this patent is extended or adjusted under 35 U.S.C. 154(b) by 0 days.

(21) Appl. No.: 16/873,320

(22) Filed: Mar. 17, 2020

(51) Int. Cl.
*A01H 5/00* (2018.01)

(52) U.S. Cl.
USPC ..... Plt./251

(58) Field of Classification Search
USPC ..... Plt./251, 263.1, 226
CPC ..... A01H 5/00
See application file for complete search history.

*Primary Examiner* — Annette H Para
(74) *Attorney, Agent, or Firm* — Cassandra Bright

(57) ABSTRACT

A new and distinct cultivar of *Hebe* plant named 'HEBANN03' is disclosed, characterized by unique variegated yellow and greyed-green foliage with purplish-pink new growth. Plants are mounded and grow wider than tall, producing racemes with trumpet shaped florets colored purple-violet. The new cultivar is a *Hebe*, suitable for ornamental garden purposes.

2 Drawing Sheets

Figure 1:
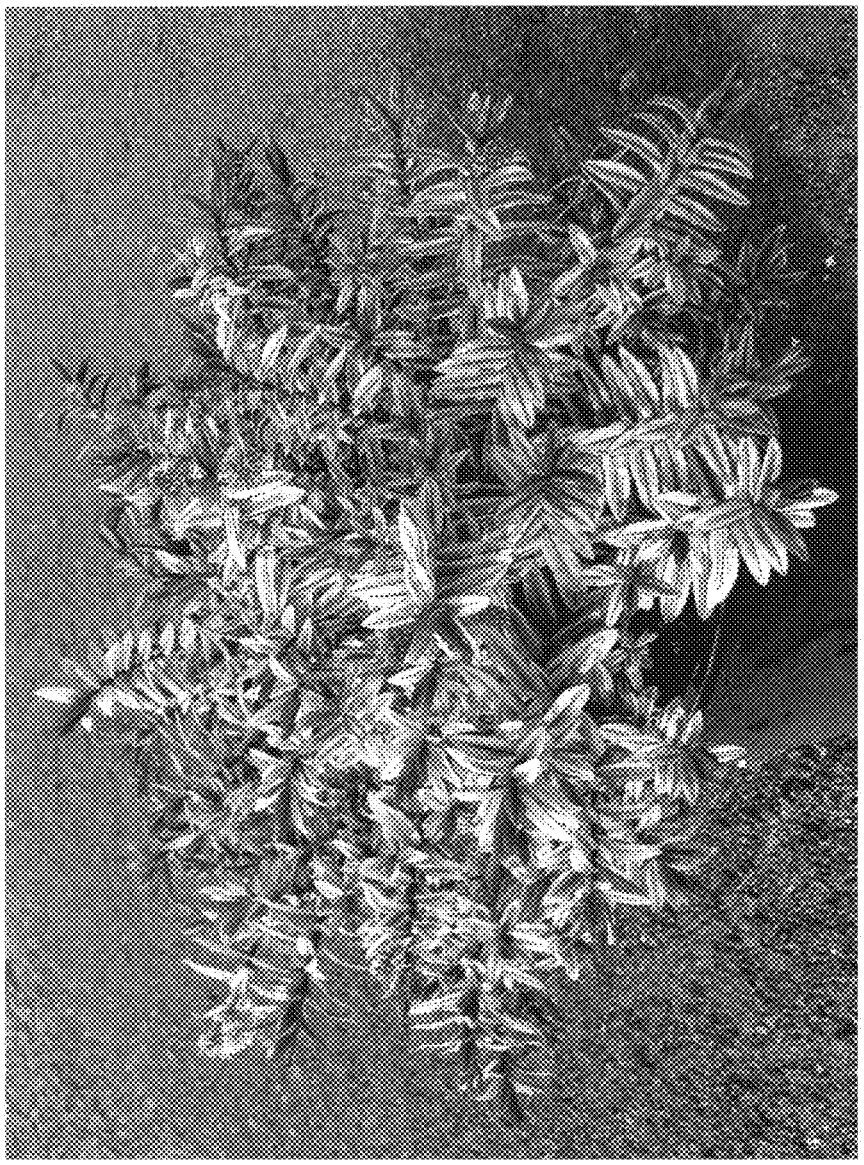

Latin name of the genus and species: *Hebe speciosa.*
Variety denomination: 'HEBANN03'.

BACKGROUND OF THE INVENTION

The new cultivar is a product of chance discovery by the inventor. This new variety, hereinafter referred to as 'HEBANN03', was discovered as a naturally occurring single branch mutation of *Hebe* 'Marilyn Monroe', unpatented. The discovery and selection of the new variety was made in 2013 at a commercial nursery in Cambridge, New Zealand.

After identifying the new variety as a potentially interesting selection, the inventor first organized propagation of 'HEBANN03' by vegetative terminal cuttings September of 2014 at the same commercial nursery in Cambridge, New Zealand. The inventor continued controlled testing and propagation, assessing stability of the unique characteristics of this variety. At least three generations have been reproduced and have shown that the unique features of this cultivar are stable and reproduced true to type. Date of first sale was Mar. 20, 2019, occurring in Australia. This sale was made directly by the inventor or one who obtained the claimed invention directly or indirectly from the inventor. This sale and all public disclosures made between Mar. 20, 2019 and the filing of this application fall within the exception allowed under 102(b)(1).

SUMMARY OF THE INVENTION

The cultivar 'HEBANN03' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'HEBANN03' These characteristics in combination distinguish 'HEBANN03' as a new and distinct *Hebe* cultivar:

1. Variegated yellow and greyed-green foliage with purplish-pink new growth.
2. Plants grow wider than tall.
3. Racemes composed of trumpet shaped florets colored violet-purple.

COMPARISON TO PARENT VARIETY

'HEBANN03' is similar in most horticultural characteristics to the parent *Hebe* 'Marilyn Monroe'. Plants of the new cultivar 'HEBANN03' however differ in the following:

1. The new variety has distinctive variegated foliage, while the seed parent has non-variegated foliage.
2. The new variety is a wider plant than the parent.

COMMERCIAL COMPARISON

'HEBANN03' can be compared to the unpatented commercial variety *Hebe* 'Annie's Winter Wonder'. Plants of the new cultivar 'HEBANN03' are similar to plants of 'Annie's Winter Wonder' in most horticultural characteristics, however, plants of the new cultivar 'HEBANN03' differ in the following:

1. Foliage of the new variety has greyed-green and yellow variegation; foliage of this comparator has green and cream variegation.

'HEBANN03' can be compared to the unpatented commercial variety *Hebe* 'Pretty n Pink'. Plants of the new cultivar 'HEBANN03' are similar to plants of 'Pretty n Pink' in some horticultural characteristics, however, plants of the new cultivar 'HEBANN03' differ in the following;

1. Foliage of the new variety is variegated, while foliage of this comparator is non- variegated.
2. The new variety is a taller plant than this comparator.

BRIEF DESCRIPTION OF THE PHOTOGRAPHS

The accompanying photograph in FIG. 1 illustrates in full color a typical plant of 'HebAnn03', in a 1 gallon pot at approximately 18 months of age.

Figure 2:
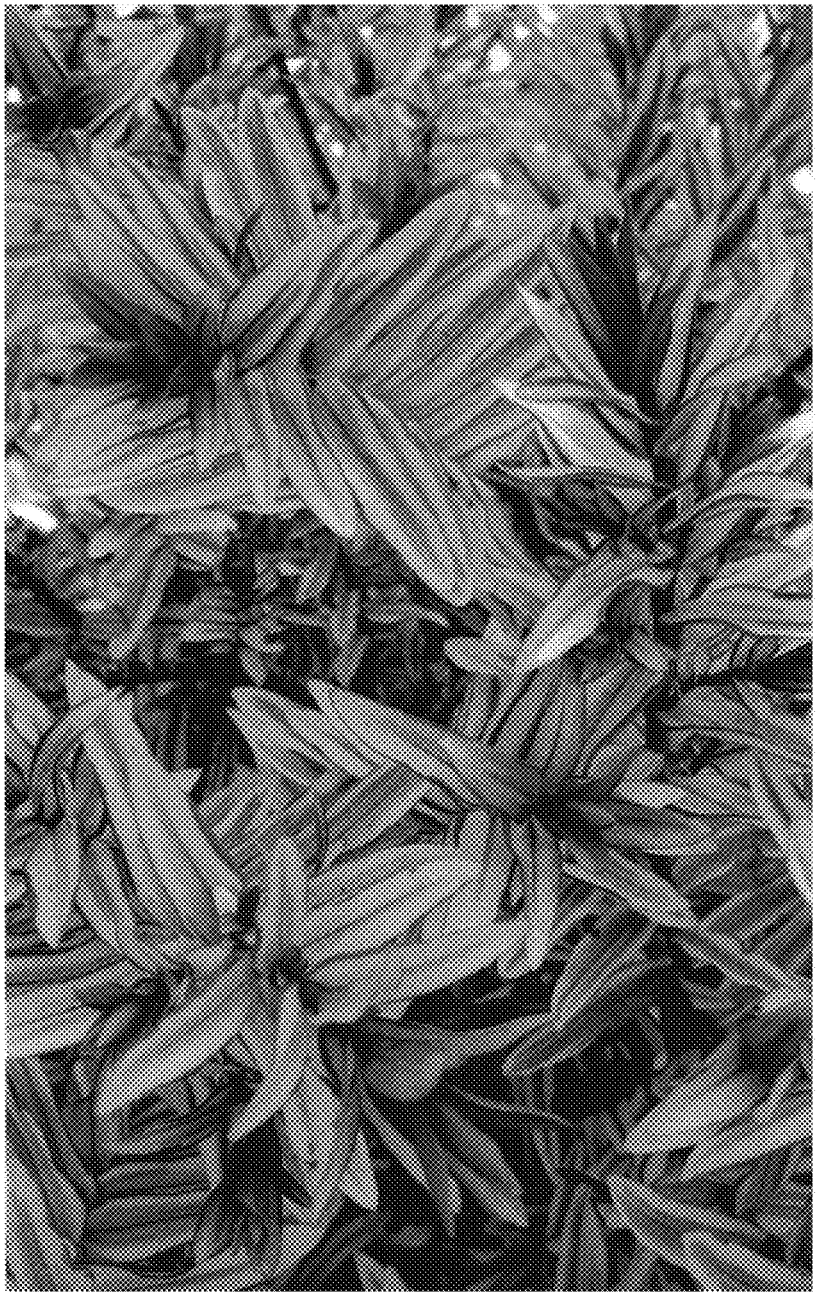

FIG. 2 illustrates in full color a close up view of foliage of the new variety.

The photographs were taken using conventional techniques and although colors may appear different from actual colors due to light reflectance they are as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'HEBANN03' plants grown outdoors in Cambridge, New Zealand. Plants are approximately 2 years old, in a 3 gallon nursery container. Measurements and numerical values represent averages of typical plant types.

Botanical classification: *Hebe* x *speciosa* 'HEBANN03'.

PROPAGATION

Typically by terminal vegetative cuttings in Spring and Summer.

Rooting: Approximately 1 month at 18° C. to initiate rooting. Approximately 3 months 18° C. to produce a rooted cutting.

Root description: Fine, fibrous young roots, well branched. Colored near RHS Grey-Brown 199A.

PLANT

Growth habit: Mounded.
Growth rate: Moderate to slow.
Height: 50 cm.
Plant spread: 70 cm.
Age of plant described: 2 years.

FOLIAGE

Leaf:
- *Type*.—Simple.
- *Arrangement*.—Opposite decussate pairs.
- *Average length*.—40 mm.
- *Average width*.—10 mm.
- *Shape of blade*.—Elliptic.
- *Apex*.—Broad acute.
- *Base*.—Truncate.
- *Attachment*.—Sessile.
- *Margin*.—Entire.
- *Texture of top surface*.—Glabrous.
- *Texture of bottom surface*.—Glabrous.
- *Color*.—Young foliage upper side: RHS Red-Purple 59B. Center streak near Greyed-Green N189A. Young foliage under side: RHS Red-Purple 59B. Center streak near Greyed-Green N189A. Mature foliage upper side: RHS Yellow 11B with Grey-Green 191A center streak. Mature foliage under side: RHS Yellow 11B with Grey-Green 191A center streak.
- *Venation*.—Indistinguishable from leaf blade.

FLOWER

Bloom period: Summer to Autumn.
Flower: Raceme, composed of trumpet shaped florets.
Inflorescence:
- *Height*.—50 mm.
- *Diameter*.—20 to 30 mm.
- *Type*.—Raceme.
- *Quantity*.—2 to 5 at upper axils.

Individual flowers:
- *Length*.—5 mm.
- *Diameter*.—5 mm.
- *Quantity*.—Average 60-70 florets per inflorescence.
- *Shape*.—Trumpet.

Petals:
- *Quantity*.—4.
- *Length*.—3 mm.
- *Width*.—Approximately 1-2 mm.
- *Apex*.—Rounded.
- *Base*.—Fused.
- *Shape of petal*.—Oblong.
- *Petal margin*.—Entire.
- *Petal arrangement*.—Rotate, base fused.
- *Petal texture*.—Smooth, glabrous all surfaces.
- *Color*.—Outside: RHS Purple-Violet N80B. Inside: RHS Purple N80D.

Pedicle:
- *Length*.—2 mm.
- *Diameter*.—2 mm.
- *Color*.—Near RHS Red-Purple 72B.
- *Texture*.—Glabrous.
- *Aspect*.—Straight.
- *Strength*.—Moderately sturdy.

Bud:
- *Shape*.—Ovate.
- *Length*.—1 mm.
- *Diameter*.—1 mm.
- *Color*.—RHS Purple N79B.

Sepals:
- *Quantity per flower*.—4 or 5.
- *Shape*.—Ovate.
- *Length*.—1 mm.
- *Width*.—1 mm.
- *Apex*.—Acute.
- *Base*.—Fused.
- *Margin*.—Entire.
- *Texture*.—Glabrous.
- *Color*.—Inner Surface: Near RHS Greyed-Green 191A. Outer Surface: Near RHS Greyed-Green 191A.

Fragrance: None.

REPRODUCTIVE ORGANS

Stamens:
- *Number*.—2.
- *Filament*.—Length: 9 mm. Color: RHS Purple-Red 186C.
- *Anthers*.—Length: About 1 mm. Shape: Heart. Color: RHS Purple-Red 71A. Pollen: Quantity: Moderate. Color: RHS Yellow 18B.

Pistil:
- *Number*.—1.
- *Length*.—8 mm.
- *Color*.—RHS Purple N77B.
- *Style*.—Length: 5 mm. Color: RHS Purple N77B.

OTHER CHARACTERISTICS

Disease and pest resistance: Moderate resistance to normal diseases and pests of *Hebe*. Mildew during wet periods.

Temperature tolerance: Cold hardy to −3° C. Ideal growing temperature 10-28° C.

Fruit/seed production: Not observed to date.

What is claimed is:

1. A new and distinct cultivar of *Hebe* plant named 'HEBANN03' as herein illustrated and described.

* * * * *